US012491101B2

(12) United States Patent
Ruetenik

(10) Patent No.: US 12,491,101 B2
(45) Date of Patent: Dec. 9, 2025

(54) KNEE DISTRACTOR APPARATUS AND METHOD

(71) Applicant: Monty L. Ruetenik, Clear Lake Shores, TX (US)

(72) Inventor: Monty L. Ruetenik, Clear Lake Shores, TX (US)

(73) Assignee: Monty L. Ruetenik, Clear Lake Shores, TX (US)

( * ) Notice: Subject to any disclaimer, the term of this patent is extended or adjusted under 35 U.S.C. 154(b) by 438 days.

(21) Appl. No.: 18/091,593

(22) Filed: Dec. 30, 2022

(65) Prior Publication Data

US 2023/0145877 A1 May 11, 2023

Related U.S. Application Data

(63) Continuation-in-part of application No. 16/919,810, filed on Jul. 2, 2020, now abandoned, and a continuation-in-part of application No. 15/727,738, filed on Oct. 9, 2017, now abandoned.

(51) Int. Cl.
*A61F 5/01* (2006.01)
*A61F 5/048* (2006.01)

(52) U.S. Cl.
CPC ............ *A61F 5/0123* (2013.01); *A61F 5/048* (2013.01); *A61F 2005/0158* (2013.01); *A61F 2005/0165* (2013.01); *A61H 2201/1246* (2013.01); *A61H 2201/1642* (2013.01)

(58) Field of Classification Search
CPC .................... A61F 5/0123; A61F 5/048; A61F 2005/0158; A61F 2005/0165; A61F 5/0111; A61F 5/012; A61F 5/042; A61F 5/05816; A61F 5/0106; A61H 2201/1246; A61H 2201/1642; A61H 2201/1238; A61H 2201/1409; A61H 2201/165; A61H 2201/1664; A61H 2201/1676; A61H 2201/5071; A61H 1/024
See application file for complete search history.

(56) References Cited

U.S. PATENT DOCUMENTS

| | | | | | |
|---|---|---|---|---|---|
| 5,337,737 | A * | 8/1994 | Rubin | A63B 23/1281 | 482/111 |
| 5,547,464 | A * | 8/1996 | Luttrell | A61H 1/024 | 482/111 |
| 5,672,152 | A | 9/1997 | Mason et al. | | |
| 5,827,208 | A | 10/1998 | Mason et al. | | |
| 7,235,059 | B2 | 6/2007 | Mason et al. | | |
| 9,474,675 | B2 | 10/2016 | Hansen | | |
| 2015/0051527 | A1* | 2/2015 | Potter | A61F 5/0125 | 602/16 |
| 2015/0209214 | A1* | 7/2015 | Herr | A61H 1/0266 | 623/27 |
| 2017/0239119 | A1* | 8/2017 | Stewart | A61G 13/1245 | |

FOREIGN PATENT DOCUMENTS

| | | | | |
|---|---|---|---|---|
| WO | WO-2021149908 A1 * | 7/2021 | | A61F 5/32 |

* cited by examiner

*Primary Examiner* — Tarla R Patel
(74) *Attorney, Agent, or Firm* — Boulware & Valoir PLLC

(57) ABSTRACT

An Apparatus and method for distraction (stretching and/or straightening) of injured knee joints.

9 Claims, 6 Drawing Sheets

KNEE DISTRACTOR APPARATUS AND METHOD

CROSS-REFERENCE TO RELATED APPLICATION

This application is a continuation in part of U.S. patent application Ser. No. 16/919,810, filed Jul. 2, 2020, which is in turn a continuation in part of U.S. patent application Ser. No. 15/727,738 filed Oct. 9, 2017 and claims the benefit and priority from U.S. Provisional Patent Application 62/407,783, filed Oct. 13, 2016, the contents and disclosure of both are incorporated herein by reference for all purposes.

BACKGROUND

Field

Apparatus and method for distraction (stretching and/or straightening) of injured knee joints.

Background

After knee surgery and in rehabilitation of sore and injured knees, it is important to distract (stretch or uncouple) the knee joint to prevent stiffness from becoming permanent. In athletes, this is frequently accomplished by having a trainer pull on the leg to distract the knee joint for a predetermined time period—10 to 20 minutes is customary. In some rehabilitation and physical therapy situations, bungee cords are attached to the ankle or a leg that has an injured knee, while the patient lies down with the cord under tension—stretching or uncoupling the knee joint. Bungee cords of varying elasticities allow customization of the tension applied. These methods, however, either require manual assistance or a controlled environment (therapy session) to be satisfactorily applied. A detailed description of the problems in knee rehabilitation and the need for stretching is described in published application U.S. 2014/0088466, together with a complicated apparatus for use in therapy, the disclosure of which is incorporated herein by reference.

DETAILED DESCRIPTION

In broad aspect, the invention is an apparatus and method for distraction (stretching and/or straightening) of injured or repaired knee joints. The apparatus comprises pneumatic or hydraulic cylinders that are designed to be disposed on either side of a leg with a knee to be treated. It is important that a cylinder be placed on each side of the leg to prevent equalize the pull on the knee joint. If only on one side it is likely that the knee would be pulled sidewise as well as downward. Cylinders are attached to a knee brace or other leg-holding device, secured above the knee joint, and attached to another device secured around the ankle of the leg. The leg-holding device and ankle device are not connected nor hinged together. When the cylinder is activated, (piston extended) the knee brace and ankle device are separated (moved apart) thus causing the knee joint to be straightened or slightly separated.

Figure 1A:
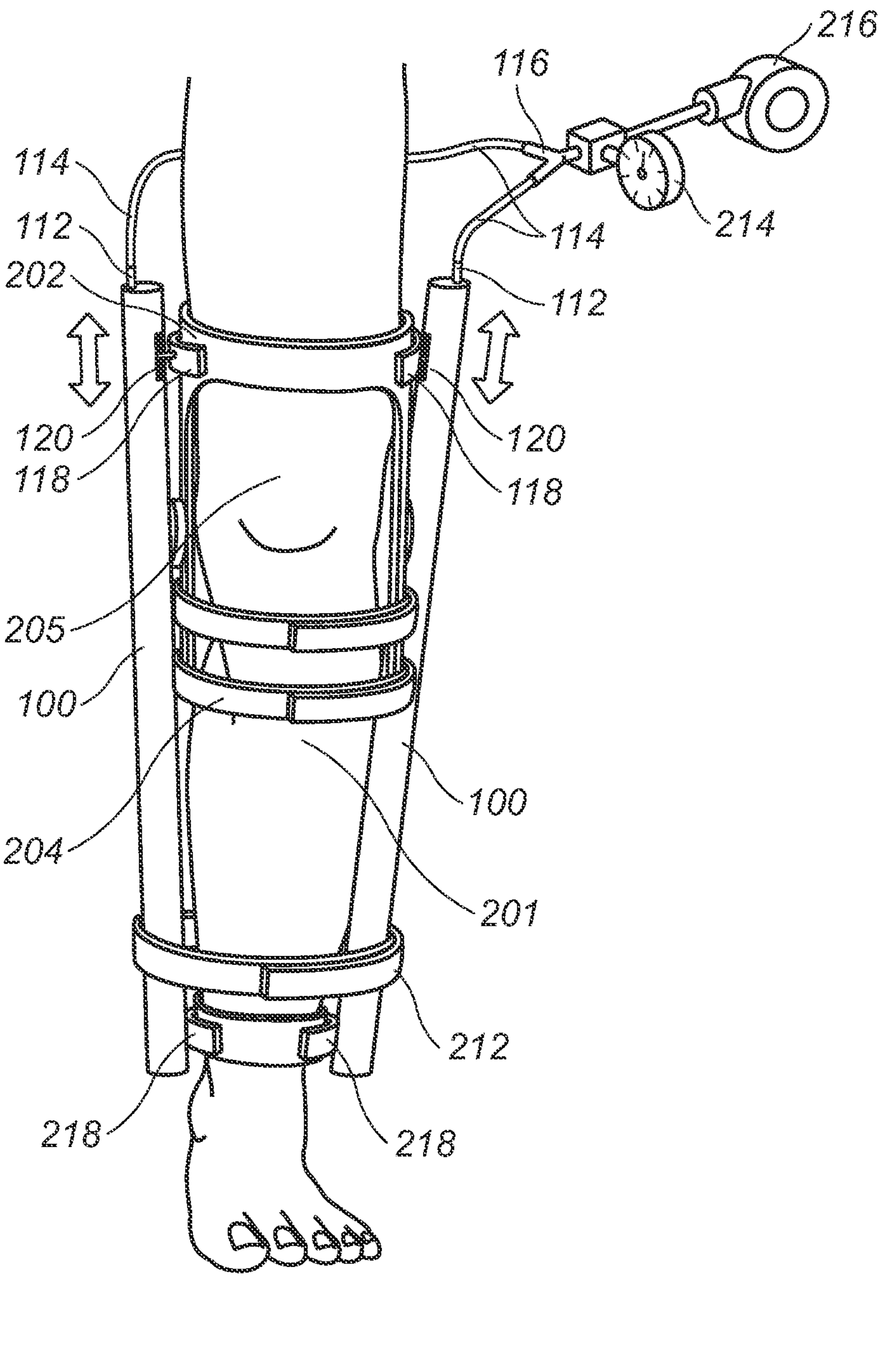
FIG. 1A is a front drawing of an embodiment of the invention showing the knee distractor in position on a leg.
Figure 1B:
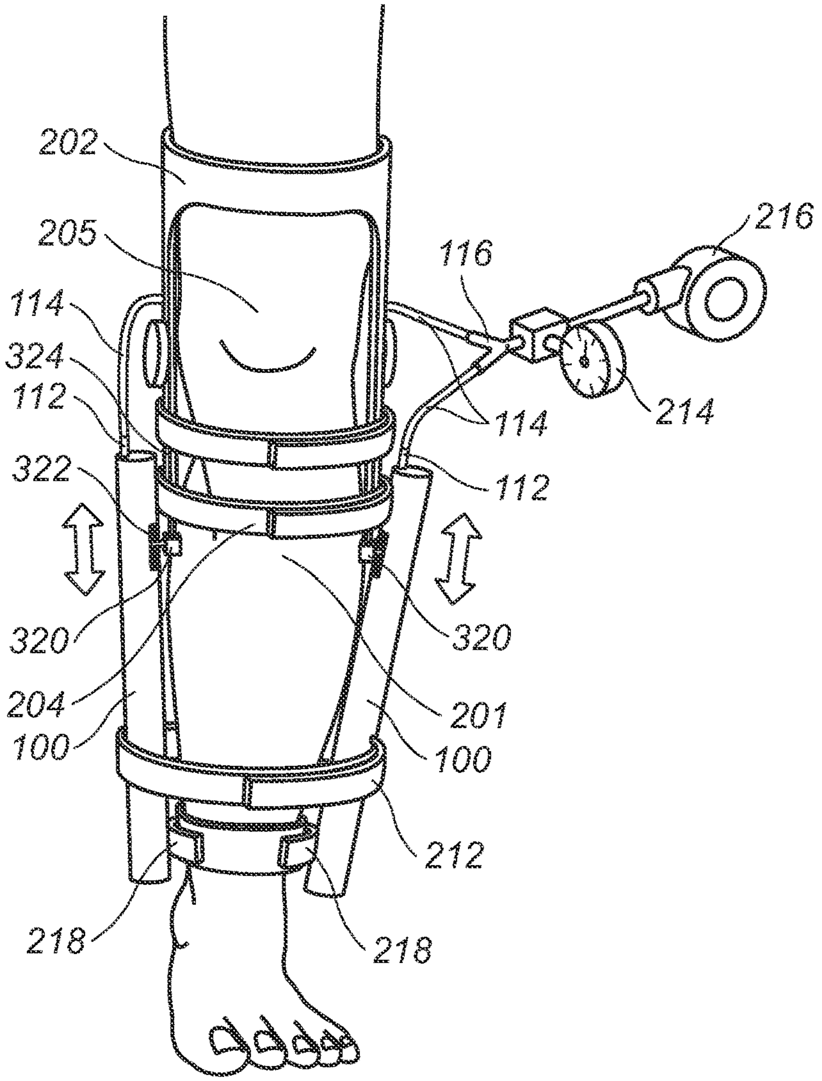
FIG. 1B is a front drawing of another embodiment of the invention showing the knee distractor in position on a leg.
Figure 1C:
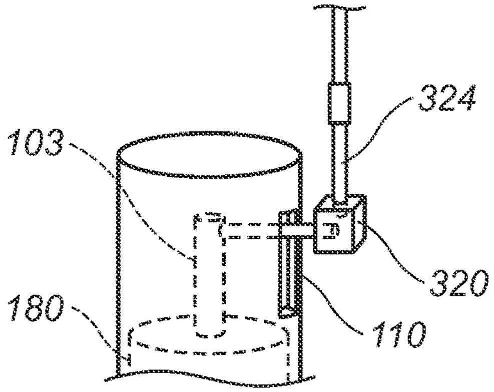
FIG. 1C is a front drawing of another embodiment of the invention showing details of the connection between the knee and cylinder tube.
Figure 2:
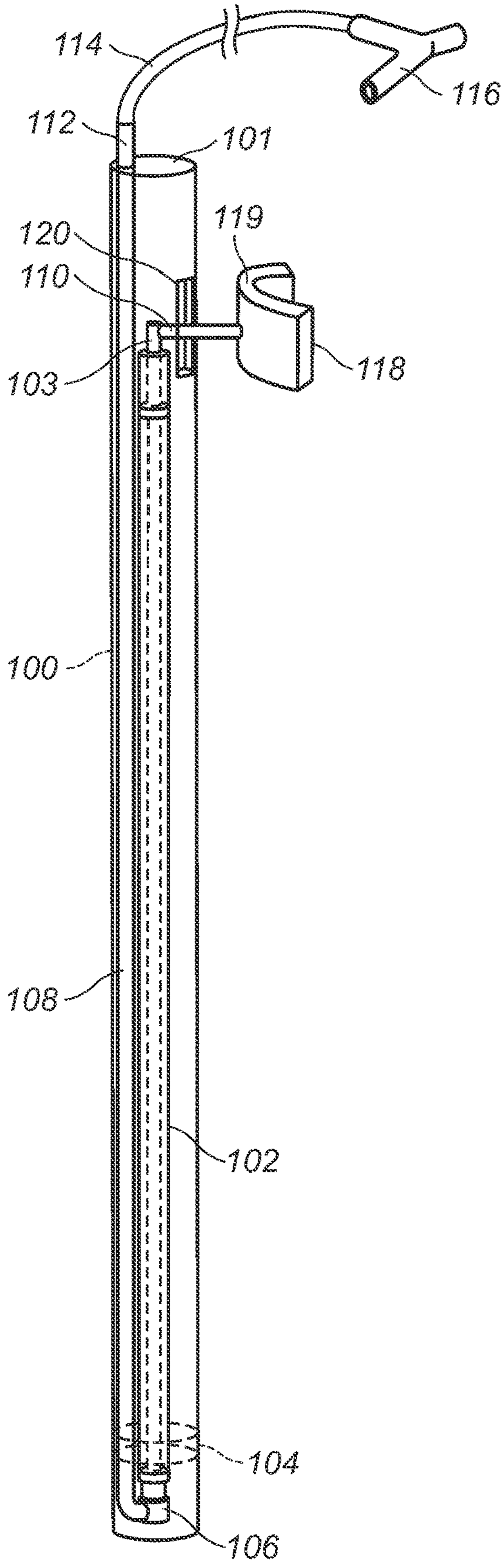
FIG. 2 is a front drawing of an embodiment of the invention showing the knee distractor components in position.

Referring to the drawings, FIG. 1A illustrates a leg 201 with a knee 205 and upper knee brace 202 and lower knee brace 204. Knee stretch cylinders 100 are attached on each side of a leg where connectors 118 are fitted with side straps on the braces 202/204. In use, the lower section of the brace 204 is loosened to allow some small movement upward, and the upper section is secured. The lower section of the tube is removably attached to an ankle brace 212 by a suitable connector, 218, (much like connector 118) and does not move during use. FIGS. 1B and 1C illustrate another embodiment of the system. In this embodiment, the piston extension 110 connects to a connection member 320 and 322 that has a slot (or other connection means) to receive a side brace of a flexion (means to set knee bend positions). It is not required that the connection 320 be able to permanently attach to brace side member 324 through 322 since the action is always upward. Rather, it is only necessary that the connection allow 110 to push brace member 324 upward in cylinder 180. This embodiment allows the brace to be set for limited movement of the knee (as often required—as to keep the knee joint from fully straightening) and be pushed upward with the knee in the limited (as for example, slightly bent) position to, for example, separate the joint members without straightening the knee joint. Patents describing flexion set means include U.S. Pat. Nos. 5,672,152, 5,827,208, and 7,235,059, the relevant disclosures of which are incorporated herein by reference. Applicant is not aware of any known current apparatus that will allow this action of extension of a bent knee joint. Conduits (such as tubing) 114 extend from the knee stretch cylinder 100 (also shown as 101) (see FIG. 2) to a Y connector 116 that is connected to the cylinder at 106 and to air pressure pump 216. Member 214 is a pressure gauge preferably a digital gauge. The gauge allows for consistent, staged, and repeated use of the device. In use in a therapy protocol, the gauge will allow return to (or alteration) of a previous treatment stretch range. FIG. 2 shows details of the knee stretch cylinder-100. The cylinder 100 comprises a straight, unitary, unhinged, hollow tube (such as a carbon or metal tube) 108 in which is disposed a straight unhinged unitary mechanical pneumatic cylinder 102 with an air connector 112 at the bottom and air hose 114 extending from the air hose connector 112 up through the open top of the tube. It is important the hollow tube and cylinder be configured so as not to bend in use so that the extension of the leg will be properly accomplished. The pneumatic cylinder is attached to the lower section of the tube at point 104. It is preferred that the pneumatic cylinder be spring-loaded so that when no air pressure is applied, it will return to its starting position. The pneumatic (or hydraulic) cylinder has a piston 103 and a horizontally (at right angles to the length of the cylinder) arranged rod 110 that extends through a slot 120 in the tube 108. The rod is connected to a brace connector 118, a semicircular member that has a slot 119 into which fits a side arm of a knee brace. When the pneumatic cylinder is activated, the piston moves upward causing the rod and therefore the connector 118 to move upward putting tension between the upper brace and ankle brace, thus stretching the knee joint. In general, the slot 120 and therefore the travel of the rod upward will be about 1 to 4 inches, with 1 to-2 inches preferred. The air hoses 114 that feed the pneumatic cylinder are connected to flexible conduits 114 that are connected by a Y connector 116 to air pump 216.

The upper knee brace is secure so that when the piston is extended, the space between the ankle brace 212 and the upper knee brace 202 is likewise extended putting tension on the knee joint and thereby stretching it. This accomplishes the desirable uncoupling or straightening of the joint-if the knee is bent, the action will tend to straighten it, and if the knee is straight, the action will uncouple or distract the joint.

Figure 4:
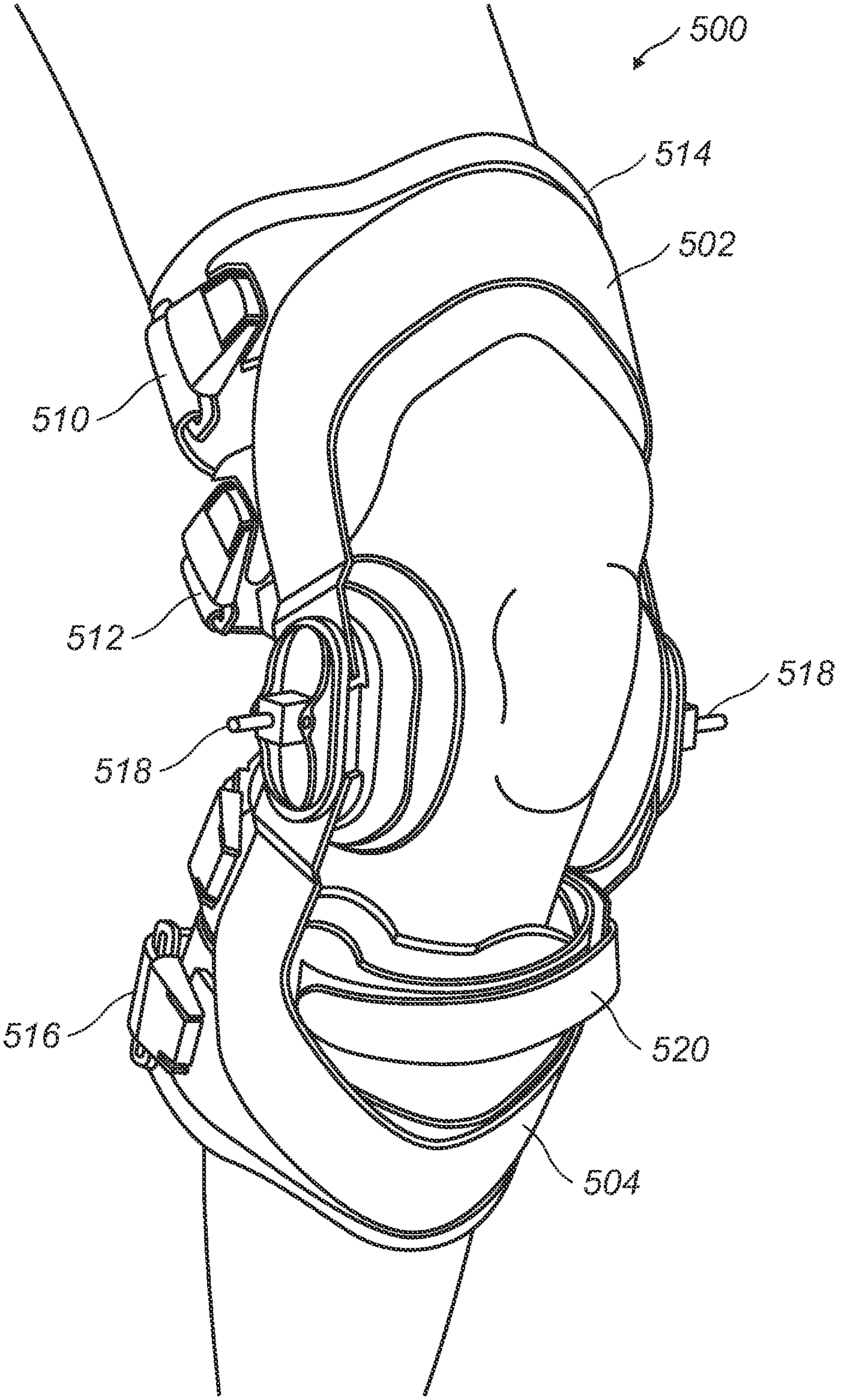
FIG. 4 is a perspective view of a knee brace suitable for of an embodiment of the invention.

FIG. 4 is an illustration of a suitable knee brace. There is a connection (118 to 518 on each side of the brace) attaching the cylinder tube (as 100 in FIG. 1) to the vertical side straps, 502, of the brace, which generally are only required to hold the strap in upward movement. Additionally, there are leg wrap bands 514 that can be latched via 510, 512 and 516 to tighten the brace 500 around the leg above and below the knee 205. Hook and loop straps 520 and 504 are also used to secure the brace to the leg. Reaction braces from Don-Joy™ can be adapted to be very suitable. In use, the knee brace will be loosened below the knee 205 to allow the more secure top section above the knee to be pushed upward by the cylinder action, thus extending the distance between the knee and ankle and ultimately distracting the knee joint.

Figure 3A:
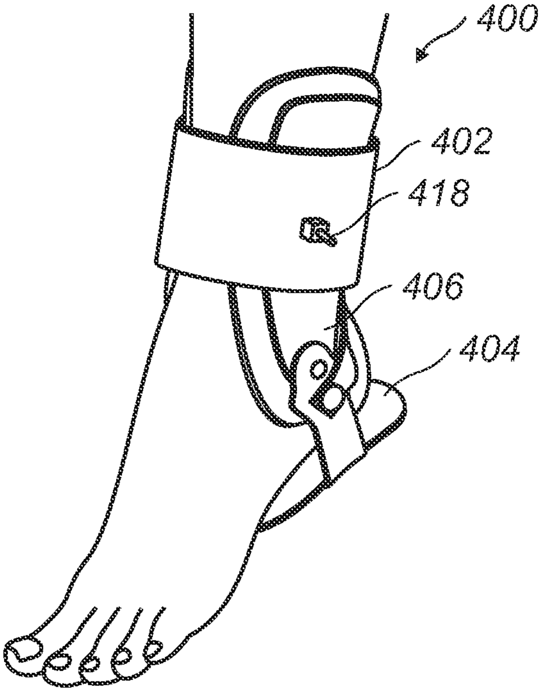
FIG. 3A is a perspective view of an ankle brace suitable for an embodiment of the invention.
Figure 3B:
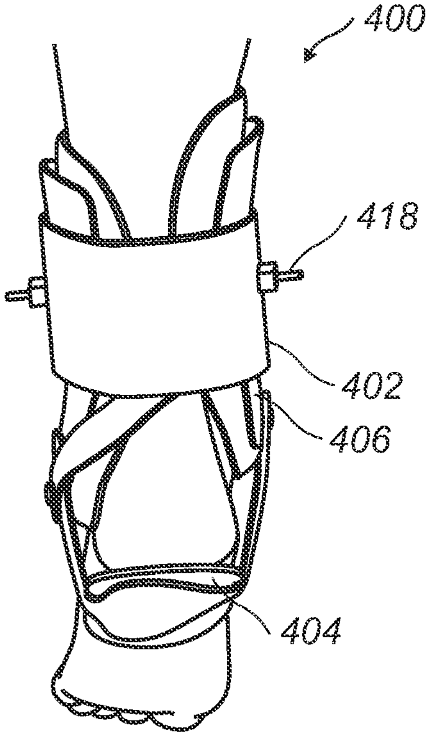
FIG. 3B is another perspective view of an ankle brace suitable for an embodiment of the invention.

FIGS. 3A and 3B illustrate a suitable ankle brace, 400. As with the knee braces, there will be a connection (218 to 418 on each side of the brace) attaching the cylinder tube (as 100 in FIG. 1) to the sides of the brace. This ankle brace has a band 402 and side pads 406 and an underfoot pad 404. Generally, it is only required to hold the brace in position to allow the ankle to be forced downward when the cylinder 100 is extended. In most ankle braces, it is preferred that the foot be placed in a shoe with the brace disposed inside the shoe, in order to ensure the connection to the ankle is secure. An ankle cuff can also be used in the same way as an ankle brace. Suitable ankle braces include T2 Multi-Sport Ankle Brace from Active Ankle™.

Suitable cylinders include those available from Automation Direct (cylinders a07020sp-9/16 bore or a07020sp-7/16 bore), preferably those with a spring return.

Suitable hand air pumps include Silverline elite hand pump model 3mitmv8510 available from ToolTopia.

Method of Use

Generally, the apparatus will be fitted by an orthotic surgeon, physical therapist, or athletic/fitness trainer. The apparatus assembly will be fitted and attached to the knee and ankle braces. When properly adjusted, the assembly is tested and characteristics plotted by measuring the extension for a given pressure applied. The air pump (or hydraulic, if used) will be applied at various pressures—e.g. 2, 5, 8, 10 psi, and the displacement (and stretch) of the piston travel (distance from knee brace attachment to ankle brace attachment) measured.

Characteristic Chart (Illustrative)

| Pressure, psi | Displacement, cm |
|---|---|
| 2 | 0.5 |
| 4 | 1.1 |
| 6 | 1.8 |
| 8 | 2.4 |
| 10 | 2.8 |
| 12 | 3.0 |
| 14 | 3.1 |

Figure 5:
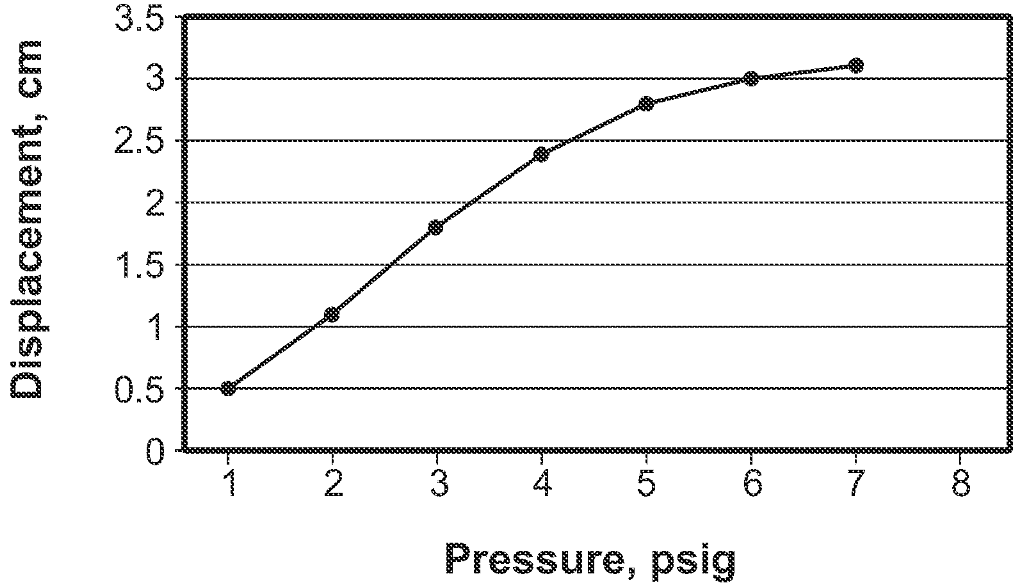
FIG. 5 is graphical plot showing relationship between displacement and applied pressure of a cylinder of an embodiment of the invention.

A characteristic curve such as illustrated in FIG. 5 can be generated for each apparatus/used combination. Using the characteristic curve, a set of user protocol can be prescribed. The user can then use the assembly at any convenient place and time without needing to visit a therapy facility.

If a knee-lock brace is used (one that locks into a predetermined position), the practitioner, physical therapist, or athletic/fitness trainer will specify (and/or set) the brace knee position lock means in the desired treatment position of the knee joint.

In the foregoing specification, the invention has been described with reference to specific embodiments thereof. It will, however, be evident that various modifications and changes can be made thereto without departing from the broader spirit and scope of the invention as set forth in the appended claims. The specification and drawings are, accordingly, to be regarded in an illustrative rather than a restrictive sense. Therefore, the scope of the invention should be limited only by the appended claims.

The invention claimed is:

1. A system for distraction of a knee joint, said system comprising:

a) an upper brace configured to attach above a knee joint;

b) a lower brace configured to attach below said knee joint;

c) a first pneumatic or hydraulic cylinder having a first extendable piston therein, said first pneumatic or hydraulic cylinder attached at a top end left side of said upper brace and attached at a bottom end left side of said lower brace;

d) a second pneumatic or hydraulic cylinder having a second extendable piston therein, said second pneumatic or hydraulic cylinder attached at a top end right side of said upper brace and attached at a bottom end right side of said lower brace;

e) said upper brace not connected to said lower brace except via said first pneumatic or hydraulic cylinder and said second pneumatic or hydraulic cylinder;

f) wherein said first pneumatic or hydraulic cylinder and said second pneumatic or hydraulic cylinder are not jointed or hinged and extend from said upper brace to said lower brace as a unitary structure; and g) a pump for activating said first pneumatic or hydraulic cylinder and said second pneumatic or hydraulic cylinder to extend said first piston and said second piston, thereby distracting said knee joint when in use.

2. The system of claim 1, wherein said first cylinder and said second cylinder are each pneumatic and said pump is an air pump fluidly coupled to said first cylinder and said second cylinder.

3. The system of claim 1, further comprising a first flexion set operably coupled to said first piston, said first flexion set for setting a desired length of piston extension, and a second flexion set operably coupled to said second piston, said flexion set for setting a desired length of piston extension.

4. The system of claim 1, wherein said first piston and said second piston are spring loaded so as to return to an unextended position when not activated.

5. The system of claim 1, wherein a degree of piston extension is controlled by pressure.

6. A method of distraction of a knee joint, said method comprising:

a) placing the system of claim 1 over a knee joint such that said upper brace is affixed above said knee joint, and said lower brace is affixed below said knee joint and said first and second pneumatic or hydraulic cylinders are disposed on a right and left side of said knee joint, respectively;

b) activating said pump thereby extending said knee joint; and c) deactivating said pump, thereby retracting said knee joint;

d) repeating steps b and c for a period of time; and e) thereafter removing said system from said knee joint.

7. A system for distraction of a human knee joint, said system comprising:

a) a knee brace configured to attach above and below a knee of a human;

b) an ankle brace configured to be attached around an ankle of said human;

c) a first pneumatic cylinder having a first extendable piston therein, said first pneumatic cylinder attached at a top end left side of said knee brace and attached at a bottom end left side of said ankle brace;

d) a second pneumatic cylinder having a second extendable piston therein, said second pneumatic cylinder attached at a top end right side of said knee brace and attached at a bottom end right side of said ankle brace;

e) said knee brace not connected to said ankle brace except via said first pneumatic cylinder and said second pneumatic cylinder;

f) wherein said first pneumatic cylinder and said second pneumatic cylinder are not jointed or hinged and extend from said knee brace to said ankle brace as a unitary structure;

g) an air-pump and pressure gauge fluidly connected to both said first pneumatic cylinder and said second pneumatic cylinder for activating said first piston and said second piston, thereby distracting said knee;

h) wherein a degree of piston extension is controlled by pressure and by a first flexion set attached to said first pneumatic cylinder and by a second flexion set attached to said second pneumatic cylinder; and i) wherein said first piston and said second piston are spring loaded so as to return to an unextended position when not activated.

8. The system of claim 7, wherein said knee brace is a resistance flexion brace.

9. A method of distraction of a knee joint, said method comprising:

a) placing the system of claim 7 on a leg of a human such that said knee brace is affixed around a bent knee of said leg, and said ankle brace is affixed around an ankle of said leg and said first and second pneumatic cylinders are disposed on a right and left side of said leg, respectively;

b) setting said first flexion set and said second flexion set to a desired amount of flexion;

c) activating said air pump to increase air pressure, thereby extending said leg; and d) releasing said air pressure, thereby retracting said leg;

e) repeating steps c and d for a period of time; and f) thereafter removing said system from said leg.

* * * * *